United States Patent [19]

Uekama et al.

[11] Patent Number: 5,854,281
[45] Date of Patent: Dec. 29, 1998

[54] PREPARATION FOR PERCUTANEOUS ABSORPTION

[75] Inventors: Kaneto Uekama; Tetsumi Irie, both of Kumamoto-ken; Michio Hara; Yasuhide Horiuchi, both of Kanagawa, all of Japan

[73] Assignee: Toray Industries, Inc., Tokyo, Japan

[21] Appl. No.: 676,250

[22] PCT Filed: Nov. 16, 1995

[86] PCT No.: PCT/JP95/02350

§ 371 Date: Dec. 10, 1996

§ 102(e) Date: Dec. 10, 1996

[87] PCT Pub. No.: WO96/15793

PCT Pub. Date: May 30, 1996

[30] Foreign Application Priority Data

Nov. 17, 1994 [JP] Japan ................................ 6-283793

[51] Int. Cl.⁶ .......................... A61K 31/34; A61K 31/19; A61K 31/20
[52] U.S. Cl. .......................... 514/468; 514/469; 514/557; 514/558; 514/560
[58] Field of Search .................... 514/468, 469, 514/557, 558, 560

[56] References Cited

U.S. PATENT DOCUMENTS 5,403,867  4/1995  Okumura et al. ...................... 514/573

FOREIGN PATENT DOCUMENTS

| 58-124778 | 7/1983 | Japan . |
| 63-211241 | 9/1988 | Japan . |
| 2-503672 | 11/1990 | Japan . |
| 3-083925 | 4/1991 | Japan . |
| 4-099719 | 3/1992 | Japan . |
| 4-164034 | 6/1992 | Japan . |
| 4-243827 | 8/1992 | Japan . |
| 5-331025 | 12/1993 | Japan . |
| 6-509346 | 10/1994 | Japan . |
| 7-252155 | 10/1995 | Japan . |
| 93 15739 | 8/1993 | WIPO . |

OTHER PUBLICATIONS

Mak et al., J. Controlled Release, 12, 67–75 (1990).
Yamashita et al., Drug Delivery System, 8, No. 4, 243–250 (1993).

*Primary Examiner*—Kimberly Jordan
*Attorney, Agent, or Firm*—Birch, Stewart, Kolasch & Birch, LLP

[57] ABSTRACT

The present invention provides a preparation for percutaneous absorption comprising as an effective component a prostaglandin $I_2$ derivative and a fatty acid or a derivative thereof, or a mixture of two or more of these, which has high percutaneous permeability of the $PGI_2$ derivative. Particularly, the present invention provides a preparation for percutaneous absorption comprising 5,6,7-trinor-4,8-inter-m-phenylene $PGI_2$ derivative and a $C_6$–$C_{24}$ fatty acid, a salt thereof or an ester thereof, or a mixture of two or more of these, which has high percutaneous permeability of the $PGI_2$ derivative. This preparation for percutaneous absorption suggests a possibility to last pharmacological effects and to reduce side effects. Thus, the preparation is expected to be used for therapy of various diseases, aiming at topical and systemic actions.

8 Claims, No Drawings

PREPARATION FOR PERCUTANEOUS ABSORPTION

This application is a 371 of PCT/JP95/02350, filed Nov. 16, 1995.

TECHNICAL FIELD

The present invention relates to a preparation for percutaneous absorption, which comprises as an effective ingredient a prostaglandin (hereinafter referred to as "PG") $I_2$ derivative. More particularly, the present invention relates to a preparation to be percutaneously absorbed, which comprises a fatty acid or a derivative thereof as an agent for enhancing percutaneous absorption, thereby percutaneous permeability of the $PGI_2$ derivative is enhanced.

BACKGROUND ART

PGs are drugs drawing attention in various fields because they widely occur in various organs and body fluids and because they exhibit strong physiological activities in a small amount. Among the PGs, $PGI_2$ has a strong activity to inhibit platelet aggregation and a strong vasodilation activity, so that use of $PGI_2$ as therapeutic agents for various diseases is expected.

However, since PGs including $PGI_2$ are very unstable chemically, the administration route is limited to intravenous administration or the like. Thus, studies are now being made for developing a stable derivative thereof and for looking for a novel administration route and administration form.

Studies of preparations to be percutaneously absorbed are also now intensively being made. Agents for enhancing percutaneous permeability of aqueous drugs are now being studied, and especially, fatty acids and terpenes are mainly studied as candidates of the agents (J. Pharm. Pharmacol., 39, 535 (1987); J. Pharm. Sci., 80, 39 (1991); Drug Des. Delivery, 1, 245 (1987); Drug Des. Delivery, 6, 229 (1990); Drug Delivery System, 6, 5 (1991); Japanese Laid-open Patent Application (Kokai) Nos. 3-261721, 2-3613 and 60-36423; and Japanese Laid-open PCT Application (Kohyo) Nos. 2-503672 and 63-502108).

On the other hand, preparations to be percutaneously absorbed, which comprise PGs such as $PGI_2$, are also now being intensively studied (Japanese Laid-open Patent Application (Kokai) Nos. 58-124778, 4-22808, 4-138187, 4-243827, 4-164034, 63-211241 and 4-312520; and Japanese Laid-open PCT Application (Kohyo) No. 6-509346).

However, these preparations for subcutaneous absorption containing $PGI_2$ derivatives do not necessarily have satisfactory percutaneous permeability.

DISCLOSURE OF THE INVENTION

The present invention provides a preparation to be percutaneously absorbed comprising a $PGI_2$ derivative as an effective ingredient and a fatty acid, a derivative thereof, or a mixture of two or more of these, which has a high percutaneous permeability of the $PGI_2$ derivative, especially a preparation to be percutaneously absorbed comprising 5,6,7-trinor-4,8-inter-m-phenylene derivative and a $C_6$–$C_{24}$ fatty acid or a salt or an ester thereof, or a mixture of two or more of these, which has a high percutaneous permeability of the $PGI_2$ derivative.

BEST MODE FOR CARRYING OUT THE INVENTION

To overcome the above-described problems, the present inventors intensively studied to discover that a preparation for subcutaneous absorption, which gives high percutaneous permeability of the $PGI_2$ derivative, is obtained by selecting a base component and an agent for enhancing percutaneous permeability, thereby completing the present invention.

That is, the present invention provides a preparation for percutaneous absorption comprising as an effective component a $PGI_2$ derivative and a fatty acid or a derivative thereof.

As the $PGI_2$ derivative which may be employed in the present invention, one having excellent stability and having platelet aggregation-inhibition activity and vasodilation activity is selected. For example, the compound of the formula (I):

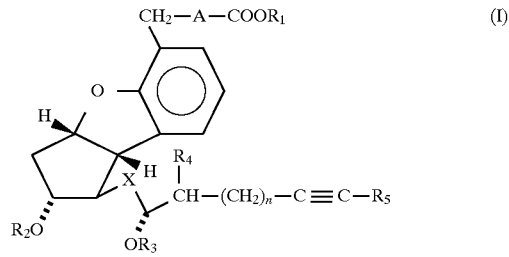

(wherein $R_1$ represents a pharmaceutically acceptable cation, hydrogen or $C_1$–$C_{12}$ linear alkyl group; $R_2$ represents hydrogen, $C_2$–$C_{10}$ acyl group or $C_7$–$C_{18}$ aroyl group; $R_3$ represents hydrogen, $C_2$–$C_{10}$ acyl group or $C_7$–$C_{18}$ aroyl group; $R_4$ represents hydrogen, methyl group or ethyl group; n represents 0 or an integer of 1 to 4; $R_5$ represents $C_1$–$C_5$ linear alkyl group; A represents i) —$CH_2$—$CH_2$— or ii) trans—CH=CH—; and X represents i) —$CH_2$—$CH_2$— or ii) trans—CH=CH—) and salts and esters thereof may be employed in the present invention.

Preferred examples of the $PGI_2$ derivative include (±)-(1R*,2R*,3aS*,8bS*)-2,3,3a,8b-tetrahydro-2-hydroxy-1-[(E)-(3S*)-3-hydroxy-4-methyl-1-octene-6-ynyl)-1H-cyclopenta[b]benzofuran-5-butyric acid (hereinafter referred to as "beraprost"), and salts and esters thereof.

The concentration of the effective ingredient in the preparation is not limited as long as it gives therapeutic effect, and may be, for example, 0.00005 to 0.1%, preferably 0.0001 to 0.05%.

Examples of the fatty acids, salts thereof and esters thereof, which may be employed as the agent for enhancing percutaneous permeability, include $C_6$–$C_{24}$ fatty acid, salts thereof and esters thereof, such as caproic acid, caprylic acid, capric acid, lauric acid, myristic acid, palmitic acid, isopalmitic acid, stearic acid, isostearic acid, arachic acid, behenic acid, lignoceric acid, myristoleic acid, palmitoleic acid, oleic acid, linoleic acid, linolenic acid, arachidonic acid, erucic acid, docosahexaenic acid and tetracosenic acid, as well as salts and esters thereof, and mixtures of two or more of these. Among these, preferred examples include $C_8$–$C_{18}$ saturated fatty acids such as caprylic acid, capric acid, lauric acid, myristic acid, palmitic acid and stearic acid; $C_{16}$–$C_{22}$ unsaturated fatty acids such as palmitoleic acid, oleic acid, linoleic acid, linolenic acid, arachidonic acid, erucic acid and docosahexaenic acid; salts and esters of these, and mixtures of two or more of these. Especially preferred examples include $C_{10}$–$C_{14}$ saturated fatty acids such as capric acid, lauric acid and myristic acid; $C_{18}$ unsaturated fatty acids such as oleic acid and linoleic acid; salts and esters of these, and mixtures of two or more of these. The content of the percutaneous permeability-enhancing agent may be, for example, 0.01 to 10% based on the total preparation. The content may preferably be 1 to 5%, more preferably 1 to 3%.

As the base, any base which is used in preparations for percutaneous absorption may be employed. Examples of the base which may be employed in the present invention include silicone oils, white vaseline, plastibase, liquid paraffin, alcohol-based bases, glycol-based bases, pressure-sensitive silicone adhesives, silicone rubbers, styrene-isobutyrene-styrene block copolymer rubbers, polyisoprene rubbers, polyisobutyrene rubbers, styrene-butadiene rubbers, butyl rubbers, natural rubbers, polyvinylalkyl ethers, poly(meth)acrylates, polyurethanes, polyamides, ethylene-vinyl acetate copolymers, alkyl acrylate-acrylic acid copolymers and hydroxypropylcellulose as well as mixtures of two or more of these. Among these, silicone oils, pressure-sensitive silicone adhesives, silicone rubbers, natural rubbers, poly(meth)acrylic acid-based adhesives and mixtures of two or more of these are preferred.

The preparation according to the present invention may comprise usable additives such as antiseptics, agents for giving adhesiveness, solubilizers, absorption co-enhancers, stabilizers and the like as required.

The preparation according to the present invention may be formulated into a formulation which can be percutaneously administered, such as ointment, liquid for external use or tape, by a conventional process.

The preparation according to the present invention is a stable and lasting preparation. By applying or attaching the preparation on the arm or chest and exchanging the preparation once or several times a day or once or several times a week, stable pharmacological effects can be obtained with high safety, so that administration of the preparation is easy.

The preparation according to the present invention aims at a topical or systemic action, and may be used as an antiulcer agent against gastric ulcer or duodenal ulcer; therapeutic agent for trauma against bedsore, burn ulcer, angiopathic ulcer, diabetic ulcer, ulcer accompanied by peripheral circulatory disturbance or hemorrhoid; antithrombotic drug against cerebral infarction, peripheral circulatory disturbance, myocardial infarction or angina pectoris; antihypertensive agent; therapeutic agent for diabetic neuropathy; drug for arteriosclerosis; drug for hyperlipidemia; therapeutic agent for hepatic diseases; or as an agent for inhibiting metastasis of malignant tumors.

EXAMPLES

The present invention will now be described in more detail referring to formulation examples. However, the present invention is not restricted by these examples.

|  | Liquid |
|---|---|
| Formulation Example 1 | |
| beraprost sodium salt | 0.5 g |
| caproic acid | 2.5 g |
| silicone oil | 500 g |
| Formulation Example 2 | |
| beraprost sodium salt | 0.5 g |
| caprylic acid | 2.5 g |
| silicone oil | 500 g |
| Formulation Example 3 | |
| beraprost sodium salt | 0.5 g |
| capric acid | 2.5 g |
| silicone oil | 500 g |
| Formulation Example 4 | |
| beraprost sodium salt | 0.5 g |

|  | Liquid |
|---|---|
| lauric acid | 2.5 g |
| silicone oil | 500 g |
| Formulation Example 5 | |
| beraprost sodium salt | 0.5 g |
| myristic acid | 2.5 g |
| silicone oil | 500 g |
| Formulation Example 6 | |
| beraprost sodium salt | 0.5 g |
| palmitic acid | 2.5 g |
| silicone oil | 500 g |
| Formulation Example 7 | |
| beraprost sodium salt | 0.5 g |
| stearic acid | 2.5 g |
| silicone oil | 500 g |
| Formulation Example 8 | |
| beraprost sodium salt | 0.5 g |
| arachidonic acid | 2.5 g |
| silicone oil | 500 g |
| Formulation Example 9 | |
| beraprost sodium salt | 0.5 g |
| oleic acid | 2.5 g |
| silicone oil | 500 g |
| Formulation Example 10 | |
| beraprost sodium salt | 0.5 g |
| linoleic acid | 2.5 g |
| silicone oil | 500 g |
| Formulation Example 11 | |
| beraprost sodium salt | 0.5 g |
| linolenic acid | 2.5 g |
| silicone oil | 500 g |
| Formulation Example 12 | |
| beraprost sodium salt | 0.5 g |
| oleic acid | 1.5 g |
| silicone oil | 500 g |
| Formulation Example 13 | |
| beraprost sodium salt | 0.5 g |
| capric acid | 1.5 g |
| silicone oil | 500 g |

The above-described liquids were prepared by dissolving 0.5 g of beraprost sodium salt in 1.5 g or 2.5 g of each fatty acid and uniformly mixing the resulting solution with 500 g of silicone oil.

|  | Ointment |
|---|---|
| Formulation Example 14 | |
| beraprost sodium salt | 0.5 g |
| capric acid | 2.5 g |
| white vaseline | 450 g |
| liquid paraffin | 50 g |
| Formulation Example 15 | |
| beraprost sodium salt | 0.5 g |
| oleic acid | 2.5 g |
| white vaseline | 450 g |
| Liquid paraffin | 50 g |
| Formulation Example 16 | |
| beraprost sodium salt | 0.5 g |
| linolenic acid | 2.5 g |
| white vaseline | 45.0 g |
| liquid paraffin | 50 g |

The above-described ointments were prepared by mixing a solution containing 0.5 g of beraprost sodium salt in 2.5 g of capric acid with 50 g of liquid paraffin and by mixing the resultant with 450 g of warmed white vaseline, followed by cooling the obtained mixture.

|  | Tape |
|---|---|
| Formulation Example 17 | |
| beraprost sodium salt | 0.5 g |
| capric acid | 2.5 g |
| pressure-sensitive silicone adhesive | 250 g |
| heptane | 250 g |
| Formulation Example 18 | |
| beraprost sodium salt | 0.5 g |
| oleic acid | 2.5 g |
| pressure-sensitive silicone adhesive | 250 g |
| heptane | 250 g |
| Formulation Example 19 | |
| beraprost sodium salt | 0.5 g |
| oleic acid | 21.5 g |
| poly(meth)acrylic acid-based adhesives | 250 g |
| Formulation Example 20 | |
| beraprost sodium salt | 0.5 g |
| oleic acid | 2.5 g |
| styrene-isobutyrene base | 250 g |

The above-described tapes were prepared as follows. First, 0.5 g of beraprost sodium salt is dissolved in 2.5 g of oleic acid and the resulting solution is mixed with an appropriate amount of a solvent. The resultant is mixed with 250 g of the adhesive base and the viscosity of the mixture is adjusted by adding a solvent. The resulting mixture is cast on a PET film and the obtained film is dried in the air.

| Formulation Example 21 | Liquid |
|---|---|
| beraprost sodium salt | 0.5 g |
| silicone oil | 500 g |
| ethanol | appropriate amount |

This liquid was prepared by dissolving 0.5 g of beraprost sodium salt in a small amount of ethanol, and uniformly mixing the resulting solution with 500 g of silicone oil, followed by evaporation of the ethanol under reduced pressure.

| Formulation Example 22 | Ointment |
|---|---|
| beraprost sodium salt | 0.5 g |
| white vaseline | 450 g |
| liquid paraffin | 50 g |
| ethanol | appropriate amount |

This ointment was prepared by dissolving 0.5 g of beraprost sodium salt in a small amount of ethanol, and mixing the resulting solution with 50 g of liquid paraffin, followed by uniformly mixing the resulting solution with 450 g of warmed white vaseline and cooling the obtained composition.

| Formulation Example 23 | Tape |
|---|---|
| beraprost sodium salt | 0.5 g |
| pressure-sensitive silicone adhesive | 256 g |
| heptane | 250 g |
| ethanol | appropriate amount |

This tape was prepared as follows. First, 0.5 g of beraprost sodium salt is dissolved in a small amount of ethanol, and the resultant is mixed with 250 g of heptane, followed by mixing the resulting solution with 250 g of the pressure-sensitive silicone adhesive. The resulting mixture is cast on a PET film and the obtained film is dried in the air.

Example 1

In vitro Percutaneous Permeation Test of Beraprost Sodium Salt Using Skin of Back of Hairless Mouse To confirm the effect of the preparations for enhancing percutaneous absorption of beraprost sodium salt, a percutaneous permeation test was carried out.

The skin excised from the back of a hairless mouse was mounted in a Loveday type diffusion cell, and each of the preparations according to Formulation Examples 1 to 11 and according to Comparative Example 1 was applied on the upper portion of the skin. Physiological saline was used as the receptor phase and the percutaneous permeation test was carried out at 25° C. The results are shown in Table 1.

As can be seen from the test results, the preparations according to Formulation Examples 1 to 11 exhibited higher percutaneous permeability than the preparation according to Comparative Example 1 in which no agent for enhancing percutaneous absorption was contained. Further, it was found that the effect for enhancing percutaneous permeability differs depending on the type of the fatty acid.

TABLE 1

Rate of Percutaneous Permeation in vitro of Beraprost through Skin of Back of Hairless Mouse

| Formulation Example | Rate of Percutaneous Permeability ($\mu$g/hr/cm$^2$) |
|---|---|
| Comparative Example 1 | 0.00 |
| Formulation Example 1 | 0.89 |
| Formulation Example 2 | 1.06 |
| Formulation Example 3 | 2.09 |
| Formulation Example 4 | 2.51 |
| Formulation Example 5 | 2.03 |
| Formulation Example 6 | 0.25 |
| Formulation Example 7 | 0.53 |
| Formulation Example 8 | 0.14 |
| Formulation Example 9 | 2.39 |
| Formulation Example 10 | 3.01 |
| Formulation Example 11 | 1.41 |

Example 2

Percutaneous Absorption Test In Vivo of Beraprost Sodium Salt Using Rats

To evaluate the transportation of beraprost sodium salt from skin to the blood circulatory system in vivo, a percutaneous absorption test was carried out using rats to confirm the effectiveness of the percutaneous absorption enhancers.

Hair was removed from the skin of back of each rat, and the tape having a size of 1 cm×1 cm formulated in accordance with Formulation Examples 17 to 19 or in accordance with Comparative Example 3 was patched. After patching the tape, blood was collected from the caudal vein at time points and blood drug level was measured.

As can be seen from the test results shown in Table 2, substantially no drug was detected in Comparative Example 3, while in cases while the tape according to Formulation Examples 17 to 19 was patched, the blood drug level was prominently high, and it was confirmed that absorption of the drug lasted.

TABLE 2

Blood Drug Level in Rats after Patching
Silicone Tape Containing Beraprost Sodium Salt

| Time Point of Blood Collection | Blood Drug Level (pg/ml) *1 | | | |
|---|---|---|---|---|
| | Comparative Example 3 | Example 15 | Example 16 | Example 17 |
| 0 hr | 0 ± 0 | 0 ± 0 | 0 ± 0 | 0 ± 0 |
| 6 hr | 0 ± 0 | 301 ± 246 | 387 ± 224 | 91 ± 90 |
| 12 hr | 14 ± 14 | 692 ± 591 | 802 ± 500 | 105 ± 125 |
| 24 hr | 0 ± 0 | 278 ± 223 | 809 ± 232 | 200 ± 132 |
| 48 hr | 19 ± 42 | 387 ± 297 | 710 ± 221 | 161 ± 110 |

*1: mean ± standard error (n = 5)

Example 3

Therapeutic Effect of Beraprost Sodium Salt Against Occlusion of Peripheral Artery in Rabbit Models Induced by Sodium Laurate To confirm the pharmacological effectiveness in vivo of the preparations according to the present invention, the effectiveness of the absorption enhancers was evaluated using rabbit models of occlusion of peripheral artery induced by lauric acid.

Hair on both ears of each male Japanese White rabbit (2.5–3.0 kg) was removed with an animal clipper. Into the auricular artery behind the right ear of each rabbit, 5 mg of sodium laurate (in 10 mM isotonic phosphate buffer, pH 7.4) was injected to induce occlusion of peripheral artery.

The preparations according to Formulation Examples 12 and 13 and according to Comparative Example 1 were tested. In each adhesive bandage (2.25 cm²) for patch test, 0.1 ml of the test preparation was impregnated, and the adhesive bandage was patched on the left ear once a day. The progress of the lesion in the right ear was observed with time and scored according to the following criteria:
Score of Lesion in Right Ear
0; normal, 1; color is changed in the tip of the ear, 2; color is changed in the entire ear, 3; necrosis occurred in the tip of the ear, 4; necrosis occurred in the entire ear, 5; deciduation of necrosed portion began.

As can be seen from the test results shown in Table 3, in the group to which silicone oil base was administered, severe occlusion of blood vessels occurred by administration of sodium laurate, and on the 7th day after the administration, color change or tissue necrosis was observed in large area in the tip of the right ear. In the group to which the preparation according to Comparative Example 1 was administered, which does not contain an absorption enhancer, the progress of the lesion was slightly prevented by the everyday administration when compared with the group to which only the base was administered.

On the other hand, in the group to which the preparations according to Formulation Example 12 or 13 containing oleic acid or capric acid as an absorption enhancer was administered, prominent inhibition of progress of the lesion was observed, due to the percutaneous absorption-enhancing effect confirmed in Examples 1 and 2. Especially, in the group to which the preparation according to Formulation Example 12 was administered, healing began to be observed at 3 days after the patching, and healed to substantially normal state at 7 days after patching.

TABLE 3

Therapeutic Effect of Beraprost Sodium Salt
Against Occlusion of Peripheral Artery in Rabbit Models
Induced by Sodium Laurate

| | Healing Score of Lesion in the Right Ear Group | | | |
|---|---|---|---|---|
| Time (day) | Administered with Base | Comparative Example 1 | Formulation Example 12 | Formulation Example 13 |
| 0 | 0.0 ± 0.0 | 0.0 ± 0.0 | 0.0 ± 0.0 | 0.0 ± 0.0 |
| 1 | 1.2 ± 0.2 | 1.0 ± 0.0 | 0.8 ± 0.0 | 0.8 ± 0.3 |
| 2 | 1.6 ± 0.2 | 1.3 ± 0.2 | 0.7 ± 0.0* | 0.8 ± 0.2* |
| 3 | 2.3 ± 0.0 | 1.8 ± 0.2 | 0.7 ± 0.2* | 1.0 ± 0.3* |
| 4 | 3.0 ± 0.3 | 2.5 ± 1.0 | 0.5 ± 0.0* | 1.2 ± 0.4* |
| 5 | 3.5 ± 0.3 | 2.5 ± 1.5 | 0.4 ± 0.1* | 1.0 ± 0.5* |
| 6 | 4.2 ± 0.1 | 2.5 ± 1.5 | 0.2 ± 0.2* | 0.8 ± 0.5* |
| 7 | 4.5 ± 0.3 | 2.5 ± 1.5 | 0.2 ± 0.2* | 0.6 ± 0.4* |

Mean of scores of healing effect ± standard deviation (N = 3).
Significant difference with respect to the group to which preparation according to Comparative Example 1 was administered:
*p < 0.05.

By the present invention, it was confirmed that $PGI_2$ derivatives can be quickly absorbed from the skin into the body by addition of a percutaneous permeation enhancer and a high blood level can be kept for a long time. Thus, by the present invention, a preparation for percutaneous absorption having high percutaneous permeability of $PGI_2$ derivatives was provided.

This suggests a possibility to last pharmacological effects and to reduce side effects. Thus, the preparation is expected to be used for therapy of various diseases, aiming at topical and systemic actions.

We claim:
1. A preparation for percutaneous absorption comprising as an effective component, a prostaglandin $I_2$ derivative; and a $C_8$–$C_{14}$ saturated or $C_{16}$–$C_{22}$ unsaturated fatty acid, a derivative thereof, a salt thereof, or mixtures thereof.
2. The preparation according to claim 1, wherein said effective component is a compound of the formula (I):

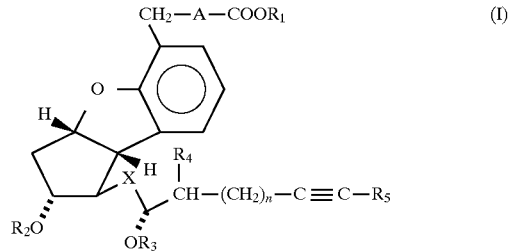

wherein
  $R_1$ represents a pharmaceutically acceptable cation, hydrogen or $C_1$–$C_{12}$ linear alkyl group;
  $R_2$ represents hydrogen, $C_2$–$C_{10}$ acyl group or $C_7$–$C_{18}$ aroyl group;
  $R_3$ represents hydrogen, $C_2$–$C_{10}$ acyl group or $C_7$–$C_{18}$ aroyl group;
  $R_4$ represents hydrogen, methyl group or ethyl group;
  n represents 0 or an integer of 1 to 4;
  $R_5$ represents $C_1$–$C_5$ linear alkyl group;

A represents —$CH_2$—$CH_2$— or trans—CH=CH—; and

X represents —$CH_2$—$CH_2$— or trans—CH=CH— or a salt or an ester thereof.

3. The preparation according to claim 1, wherein said prostaglandin $I_2$ derivative is (±)-(1R*,2R*,3aS*,8bS*)-2,3,3a,8b-tetrahydro-2-hydroxy-1-[(E)-(3S*)-3-hydroxy-4-methyl-1-octene-6-ynyl)-1H-cyclopenta[b]benzofuran-5-butyric acid; or a salt or an ester thereof.

4. The preparation according to claim 1, wherein said saturated fatty acid is caprylic acid, capric acid, lauric acid, myristic acid, and said unsaturated fatty acid is palmitoleic acid, oleic acid, linoleic acid, linolenic acid, arachidonic acid, erucic acid or docosahexaenic acid.

5. The preparation according to claim 1, wherein said fatty acid or a derivative thereof is a $C_{10}$–$C_{14}$ saturated fatty acid, $C_{18}$ unsaturated fatty acid, a salt thereof, or a mixture of two or more of these.

6. The preparation according to claim 5, wherein said saturated fatty acid is capric acid, lauric acid or myristic acid, and said unsaturated fatty acid is oleic acid or linoleic acid.

7. The preparation according to claim 1, wherein said fatty acid is a $C_{10}$–$C_{14}$ saturated fatty acid.

8. The preparation according to claim 1, wherein said fatty acid is a $C_{18}$ unsaturated fatty acid.

* * * * *